(12) United States Patent
Barron et al.

(10) Patent No.: US 8,217,137 B2
(45) Date of Patent: Jul. 10, 2012

(54) FULLERENE-BASED AMINO ACIDS

(75) Inventors: Andrew R. Barron, Houston, TX (US); Jianzhong Yang, Missouri City, TX (US)

(73) Assignee: William Marsh Rice University, Houston, TX (US)

( * ) Notice: Subject to any disclaimer, the term of this patent is extended or adjusted under 35 U.S.C. 154(b) by 1090 days.

(21) Appl. No.: 10/585,277

(22) PCT Filed: Jan. 14, 2005

(86) PCT No.: PCT/US2005/001187
§ 371 (c)(1),
(2), (4) Date: Dec. 2, 2008

(87) PCT Pub. No.: WO2005/070827
PCT Pub. Date: Aug. 4, 2005

(65) Prior Publication Data
US 2009/0197315 A1 Aug. 6, 2009

Related U.S. Application Data

(60) Provisional application No. 60/536,544, filed on Jan. 14, 2004.

(51) Int. Cl.
*C07C 229/02* (2006.01)
*C07K 2/00* (2006.01)
(52) U.S. Cl. .......... 530/300; 560/48; 560/116; 562/443; 562/450; 562/498
(58) Field of Classification Search .......... None
See application file for complete search history.

(56) References Cited

U.S. PATENT DOCUMENTS 7,163,956 B2 * 1/2007 Wilson et al. ................. 514/410
7,758,889 B1 * 7/2010 Sagman et al. ............... 424/489

FOREIGN PATENT DOCUMENTS
EP          919520 A2 *  6/1999
WO   WO 2004091508 A2 * 10/2004

OTHER PUBLICATIONS

Burley et al. Synthesis and Characterization of Mono- and Bis-methano[60]fullerenyl Amino Acid Derivatives . . . Journal of Organic Chemistry. 2002, vol. 67, No. 24, pp. 8316-8330.*

(Continued)

*Primary Examiner* — Jeffrey E Russel
(74) *Attorney, Agent, or Firm* — Winstead PC

(57) ABSTRACT

The present invention is directed to a series of new compounds, combining the unique properties of fullerenes and bio-active amino acid residues, and to methods for making such compounds. The present invention is directed toward fullerene-based amino acids, and to amino acid residues, peptide chains, proteins, and polypeptides made from such fullerene-based amino acids. The present invention is further directed to amino acid residues, peptide chains, proteins, and polypeptides comprising such fullerene-based amino acids and into which such fullerene-based amino acids have been incorporated. Exemplary compounds have been prepared, and these compounds have been characterized and confirmed with infrared (IR) spectroscopy, nuclear magnetic resonance (NMR) spectroscopy, mass spectrometry (MS), etc. These new compounds, which are additions to the existing amino acid residue family, may potentially possess useful pharmaceutical application and may provide a new platform for further exploration in cancer therapy, and peptide and protein engineering.

18 Claims, 12 Drawing Sheets

OTHER PUBLICATIONS

Pantarotto et al. Solid-Phase Synthesis of Fullerene-peptides. Journal of the American Chemical Society. 2002, vol. 124, No. 42, pp. 12543-12549.*

Skiebe et al. A Facile Method for the Synthesis of Amino Acid and Amido Derivatives of C60. Journal of the Chemical Society, Chemical Communications. 1994, pp. 335-336.*

An et al. Synthesis of alpha-Amino Acid Derivatives of C60 . . . Journal of Organic Chemistry. 1993, vol. 58, No. 18, pp. 4799-4801.*

Enes et al. Synthesis of [60]fullerene-based alpha-amino acid derivatives. Tetrahedron. 2005, vol. 61, pp. 1423-1431.*

Friedman et al.; J. Am. Chem. Soc., "Inhibition of the HIV-1 Protease by Fullerene Derivatives: Model Building Studies and Experimental Verification," 1993, 115:6506-6509.

Sijbesma et al.; J. Am. Chem. Soc., "Synthesis of a Fullerene Derivative for the Inhibition of HIV Enzymes," 1993, 115:6510-6512.

Yamakoshi et al.; J. Am. Chem. Soc., "Active Oxygen Species Generated from Photoexcited Fullerine ($C_{60}$) as Potential Medicines: $O_2^-$ versus $^1O_2$," 2003, 125:12803-12809.

An et al; Tetrahedron, "Sequence-Specific Modification of Guanosine in DNA by a $C_{60}$-Linked Deoxyoligonucleotide: Evidence for a Non-Singlet Oxygen Mechanism," 1996, 52, 14, 5179-5189.

Lu et al.; Tetrahedron Letters, "Novel diacid accelerated borane reducing agent for imines," 2002, 43:8617-8620.

* cited by examiner

Scheme 3

R= Boc or

Fmoc

Scheme 4

R1= OH
R2 = OtBu

```
SEQUENCE LISTING

<160> NUMBER OF SEQ ID NOS: 1

<210> SEQ ID NO 1
<211> LENGTH: 9
<212> TYPE: PRT
<213> ORGANISM: Artificial Sequence
<220> FEATURE:
<223> OTHER INFORMATION: Synthesized Peptide
<220> FEATURE:
<221> NAME/KEY: Xaa
<222> LOCATION: (1)..(1)
<223> OTHER INFORMATION: Xaa is bucky amino acid (BAA)

<400> SEQUENCE: 1

Xaa Glu Glu Glu Glu Gly Gly Gly Ser
1               5
```

FULLERENE-BASED AMINO ACIDS

CROSS-REFERENCE TO RELATED APPLICATIONS

This Application claims priority to U.S. Provisional Application Ser. No. 60/536,544, filed Jan. 14, 2004.

FIELD OF THE INVENTION

The present invention relates generally to fullerene materials, and specifically to amino acids into which such materials are incorporated.

BACKGROUND OF THE INVENTION

The incorporation of fullerenes into macromolecular structures of biological importance has been a continual pursuit of researchers over the course of the past decade. "Buckminsterfullerene," $C_{60}$, or [60] fullerene (names which all refer to the same molecule), is well known for its unique hydrophobic nature and other physiochemical properties that make it an interesting pharmocophore candidate. For instance, $C_{60}$ and other fullerenes can be incorporated into the cylindrical hydrophobic cavity (or cavities) of HIV protease and behave as an inhibitor. See Friedman et al., J. Am. Chem. Soc., 1993, 115, pp. 6506-6509. In vitro studies of water soluble-[60] fullerene derivatives containing hydrophilic functionalities show that they can inhibit acutely- and chronically-affected peripheral blood mononuclear cells with an EC50 (50% effective concentration) as low as 7 µM. See Sijbesma et al., J. Am. Chem. Soc., 1993, 115, pp. 6510-6512. Active oxygen species can be generated from photoexcited fullerenes as potential medicines. See Yamakoshi et al., J. Am. Chem. Soc., 2003, 125, pp. 12803-12809. This makes fullerenes and their derivatives excellent candidates for use in photodynamic therapy (PDT) for cancer treatment. Therefore, building bioactive [60] fullerene derivatives is not merely of scholarly interest, but also of considerable medicinal significance.

Amino acids are a basic and essential building block for living organisms at all levels. Indeed, they polymerize into polypeptides or proteins, proteins being responsible for much of the mechanistic phenomenon within biological organisms (e.g. enzymes, antibodies, ion channels, hemoglobin, etc.). The idea of combining fullerenes with amino acid residues has long been of great interest to chemists. The incorporation of fullerene-based amino acids into proteins, peptides or antibodies could lead to many new applications in the realm of medicinal chemistry. Possible interactions of fullerene with hydrophobic pocket(s), or other arene-arene interactions, within proteins or enzymes could provide new insight into the function-structure study of such proteins and enzymes. However, to build molecules with [60] fullerene as an inseparable part of the amino acid, i.e., an amino acid resembling a natural one and having the general formula:

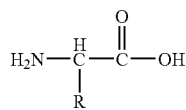

and denoted hereafter as $H_2N-CH(R)-C(O)-OH$, and which can survive through the entire biological range of pH changes and enzymatic cleavage and stay whole, remains a challenge. So far, reports of fullerene-based amino acids are still rare, and these generally contain an amide or ester link. Such linkages are susceptible to cleavage by hydrolysis. Considerable effort in fullerene chemistry has shown that this task is not trivial, since $C_{60}$ itself readily reacts with nucleophiles and also reacts under many hydrogenation conditions. The latter scenario represents a major obstacle for its use in many chemical processes. Methods and compositions that serve to overcome some of these obstacles would be very beneficial.

BRIEF DESCRIPTION OF THE INVENTION

The present invention is generally directed to a series of new compounds, combining the unique properties of fullerenes and bio-active amino acid residues, and to methods of making such compounds. In some embodiments, these new compounds are fullerene-based amino acids. In some or other embodiments, these new compounds are amino acid residues, peptide chains, proteins, and polypeptides made from such fullerene-based amino acids. Generally, such compounds can survive through the entire biological range of pH changes and enzymatic cleavage.

Amino acid residues, peptide chains, proteins, and polypeptides comprising the fullerene-based amino acids of the present invention, and into which such fullerene-based amino acids have been incorporated, may additionally comprise other naturally occurring or synthetic amino acids.

In some embodiments, the fullerene-based amino acids of the present invention comprise fullerene species that are endohedrally-doped with one or more dopant species. Such dopant species include, but are not limited to, radioactive species, non-radioactive species, metals, gases, spin ½ nuclei, and combinations thereof.

In some embodiments, the fullerene-based amino acids of the present invention are part of a synthetic protein that has a specific biological function. Such function includes, but is not limited to, enzymatic, antibody, oxygen transport, ion transport, and combinations thereof. In some embodiments, the fullerene-based amino acids are a structure-determining element in the synthetic protein. In some of these embodiments, the fullerene-based amino acids provide for reaction pockets (e.g., voids where non-aqueous chemistry can take place) within the synthetic proteins. In some or other embodiments, the fullerene-based amino acids serve as links between two or more amino acids in the protein.

In some embodiments, the present invention is directed to methods of making such above-described fullerene-based amino acids. In other embodiments, the present invention is directed at methods of incorporating or assembling these fullerene-based amino acids into amino acid residues or synthetic proteins, wherein such residues and proteins may or may not further comprise other non-fullerene-based amino acids of natural and/or synthetic origin.

These new compounds, which are additions to the existing amino acid residue family, may potentially possess useful pharmaceutical application and may provide a new platform for further exploration in cancer therapy, and peptide and protein engineering.

The foregoing has outlined rather broadly the features of the present invention in order that the detailed description of the invention that follows may be better understood. Additional features and advantages of the invention will be described hereinafter which form the subject of the claims of the invention.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION OF THE INVENTION

Figure 1:
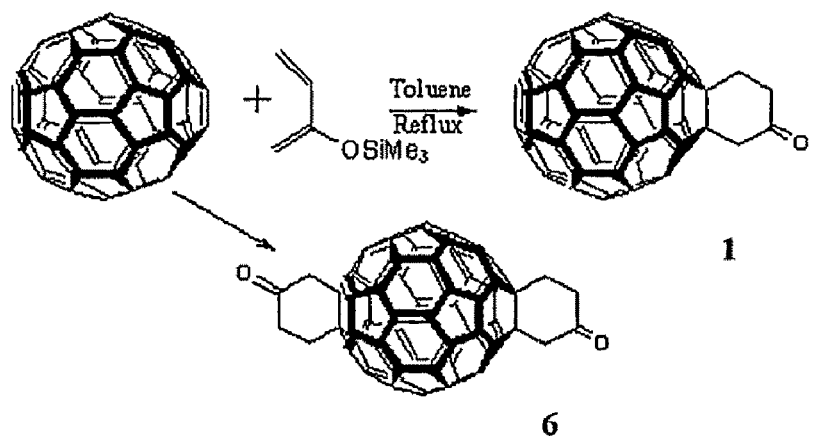
FIG. 1 depicts reaction Schemes 1 and 2.
Figure 1:
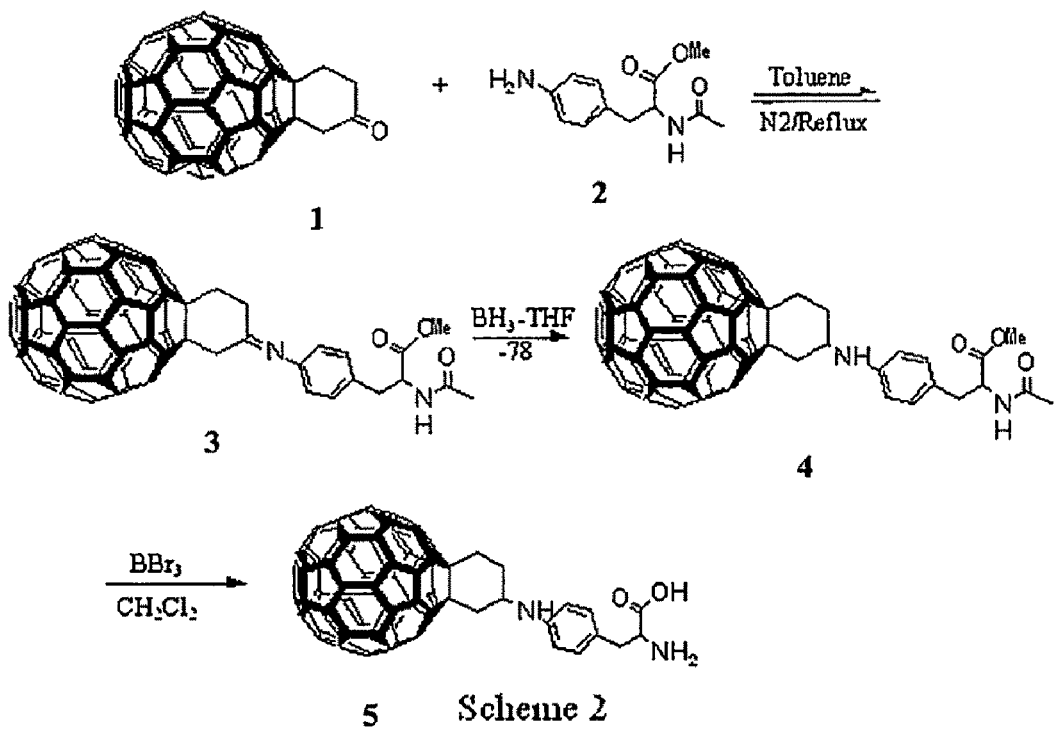

The present invention is directed to a series of new compounds, combining the unique properties of fullerenes and bio-active amino acid residues, and to methods for making such compounds. The present invention is directed toward fullerene-based amino acids, and to amino acid residues, peptide chains, proteins, and polypeptides made from such fullerene-based amino acids. The present invention is further directed to amino acid residues, peptide chains, proteins, and polypeptides comprising such fullerene-based amino acids and into which such fullerene-based amino acids have been incorporated. Exemplary compounds have beep prepared, and these compounds have been characterized and confirmed with infrared (IR) spectroscopy, nuclear magnetic resonance (NMR) spectroscopy, mass spectrometry (MS), etc. These new compounds, which are additions to the existing amino acid residue family, may potentially possess useful pharmaceutical application and may provide a new platform for further exploration in cancer therapy, and peptide and protein engineering.

Nano- or fullerene-based amino acids (terms used synonymously herein), according to the present invention, are amino acids having the general formula:

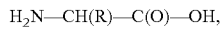

wherein a fullerene is, or is part of, the "R" group.

A peptide or peptide chain, according to the present invention, is a compound comprising two or more amino acids. A polypeptide is a polymer of amino acids linked through peptide bonds. A protein is a polypeptide of biological significance.

Fullerenes, according to the present invention, can be traditional fullerenes (e.g., $C_{60}$, $C_{70}$, $C_{82}$, $C_{84}$, etc.), but they can also be buckytubes (carbon nanotubes) and buckyonions (nested fullerenes). They can be doped (e.g., metallofullerenes such as $La@C_{60}$), and/or they can be derivatized with other substituents to alter their chemical and physical properties.

A nano-amino acid (fullerene-based amino acid) and its corresponding residue may be synthesized through a number of routes. For example, the condensation of 1,2-4'cyclohexanonefullerene with 4-aminophenylalanine, followed by hydrogenation with $BH_3$-THF and de-protection with $BBr_3$ yields a nano-amino acid that has been christened "Ricene."

Nano-amino acids may find use as drugs or similar pharmaceutical agents. Furthermore, since amino acids and their residues can remain chemically active, nano-amino acids may be incorporated into typical poly-amino acid macromolecules such as proteins. In some embodiments, the nano-amino acid may replace a naturally occurring amino acid in a protein chain to alter the function or binding of that protein. When combined with other agents, it could function as a vehicle for drug or radioactive ray delivery in cancer therapy. This type of nano-amino acid and residue also provides a new platform for further extending such chemistry.

As previously mentioned, in some embodiments, in place of simple fullerenes, it is possible to use metal-doped fullerenes (metallofullerenes), in which the metal has a secondary function such as electron spin or radioactive decay that provides an alternative or additional function to the nano-amino acid and/or residue of which it is a part. Such species could be useful for cancer treatment and/or diagnostic imaging. As an example, a metallofullerene comprising a metal of appropriate nuclear spin could be incorporated into a fullerene-based amino acid, which in turn is incorporated into a protein antibody. If this antibody is chosen so as to target specific cells (e.g., cancer cells), these cells, or agglomerations of these cells, can be imaged more readily. Alternatively, such a modified antibody could be made to deliver radioactive or cytotoxic material to cancer cells, thereby providing a therapeutic role.

While some fullerene-based amino acid residues have been previously synthesized, all of these have had an ester or amide link between the fullerene and amino acid residue, which preclude them from being true amino acid residues. In other words, they are a reaction product of an amino acid and a fullerene. Put forth herein are the first-ever fullerene-based amino acids that resemble and behave as a natural amino acids having the general formula:

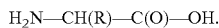

To produce the nano-amino acids and amino acid residues of the present invention, some known fullerene chemistry is used to generate a starting material that can undergo further reaction. The pioneering work of Rubin and coworkers on the Diels-Alder reaction of $C_{60}$ with 2-trimethysiloxyl silane 1,3-butadiene provides an excellent starting point for further functionalization of $C_{60}$ as shown in FIG. 1 (Scheme 1). See Rubin et al. Tetrahedron, 1996, 52(14), pp. 5179-5189. Since the ketone functionality is a very reactive functional group, reaction of buckyketone 1 can lead to a series of fullerene derivatives with potential medicinal applications.

Figure 4:
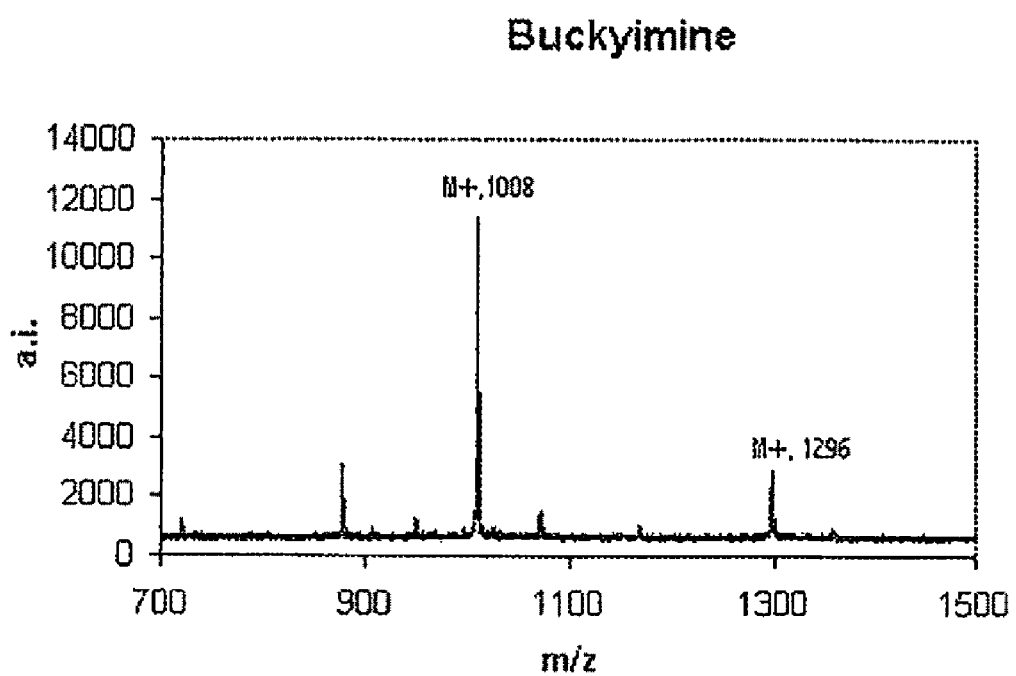
FIG. 4 depicts a MDI-TOF mass spectrum of buckyimine 3.

As shown in FIG. 1 (Scheme 2), buckyimine 3 can be produced via the condensation of 1 with 4-amine-(N—Ac) Phe-OMe 2. Thereafter, hydrogenation of the imine 3 leads to a protected fullerene-based amino acid. The final amino acid can then be prepared by a deprotection method to yield a fullerene-based phenylalanine analog 5 without an amide or ester link. This route can be used as a facile and versatile method for preparing a wide range of fullerene-based amino acids Referring again to Scheme 2, the nucleophilic addition of buckyketone 1 and N—Ac-(4-amino)-Phe-OMe 2 readily leads to the formation of the buckyimine 3, as characterized and confirmed by matrix-assisted laser desorption time-of-flight (MALDI-TOF) mass spectrometry (MS). See FIG. 4. The imine intermediate has not been further characterized, as it readily decomposes on the silica-gel column during purification. It is worth noting, however, that the buckyimine 3 parent ion is stable under the operational conditions of MALDI-TOF-MS, while its reduced form is not.

Figure 5:
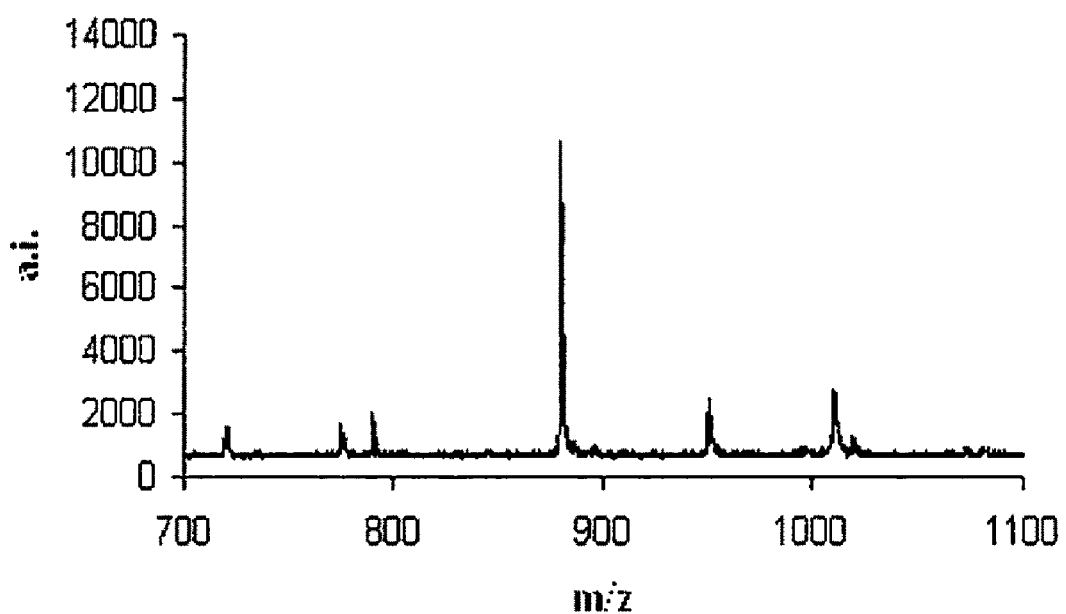
FIG. 5 depicts a MALDI-TOF mass spectrum of buckyaminoacid 5 showing fragmentation of the molecular ion.

Conversion of the Schiff base [imine] to the corresponding amine can be achieved by di-acid catalyzed $BH_3$-THF reduction at $-78°$ C. followed by conventional work up under basic conditions. While hydrogenation of 4 can be carried out using a number of methods, an exemplary method involves the reaction of the N—Ac amino ester with $BBr_3$. This leads to the formation of the deprotected amino acid 5, as characterized by MALDI-TOF-MS, the conditions for which typically lead to significant fragmentation, as shown in FIG. 5.

It is worth noting that the reaction of fullerenes with 2-trimethylsilane 1,3-butadiene also produce a bis-adduct, but with two cyclohexagonal ketone rings. These also react with APAM [4-amine-(N—Ac)-Phe-Ome] to produce a bis phenyalanine with a fullerene linkage, as identified by MALDI-TOF-MS. Therefore, it is possible to make di-amino acids with fullerene species serving, for example, as an S—S unit between cystines.

The N—Ac amino ester and its deprotected form have been fully characterized by $^1H$ and $^{13}C$ NMR. Such studies reveal that the introduction of a phenylalanine moiety increases the energy barrier for the inversion of hexagonal ring, and that the $CH_2$ groups are well resolved even at room temperature. Upon deprotection of the acetyl and methyl groups, there is a significant change in the chemical shift of the single hydrogen on the α carbon that moves to higher field and partially overlaps with the tertiary hydrogen on the hexagonal ring.

The fullerene-based amino acid 5 meets the general formula requirements for an amino acid. Furthermore, its linkage of the R group, comprising the fullerene species, to the amino acid backbone is immune to hydrolysis under typical biological conditions. These two attributes alone distinguish the nano-amino acids of the present invention over the prior art.

Figure 2:
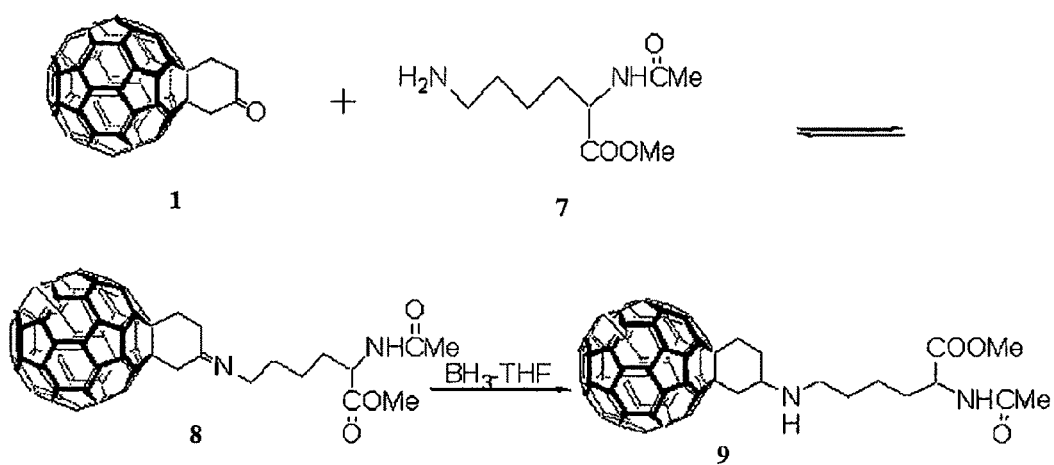
FIG. 2 depicts reaction Scheme 3.
Figure 3:
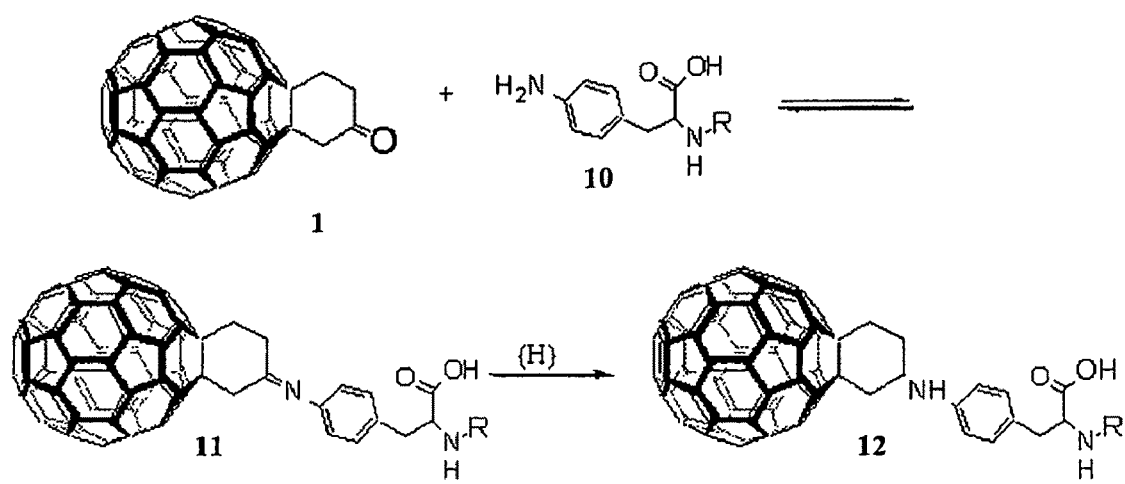
FIG. 3 depicts reaction Scheme 4.
Figure 6:
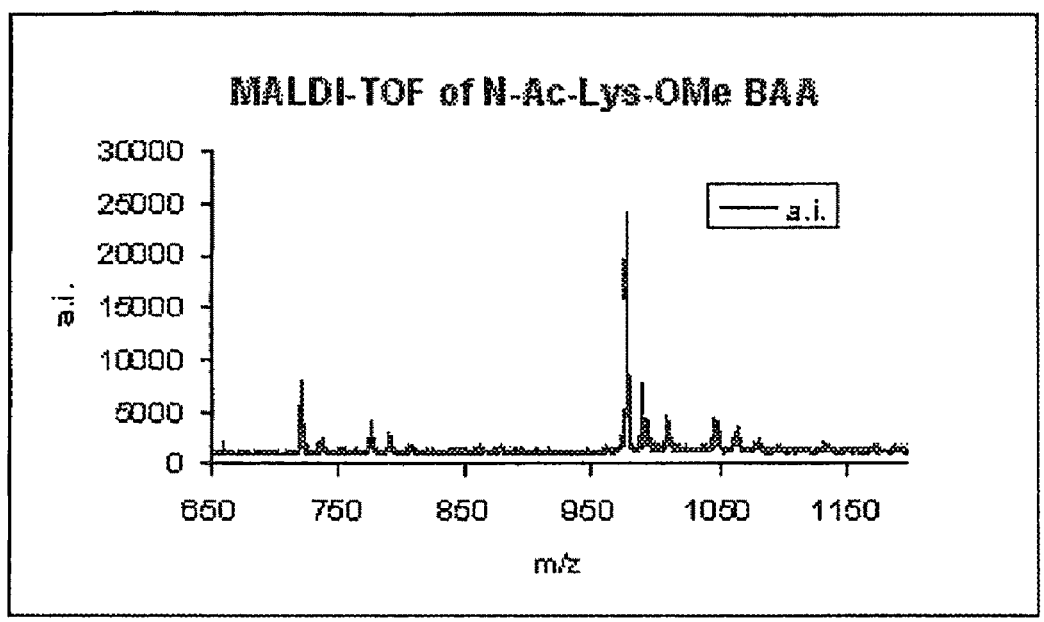
FIG. 6 depicts a MALDI-TOF mass spectrum of 9.
Figure 7:
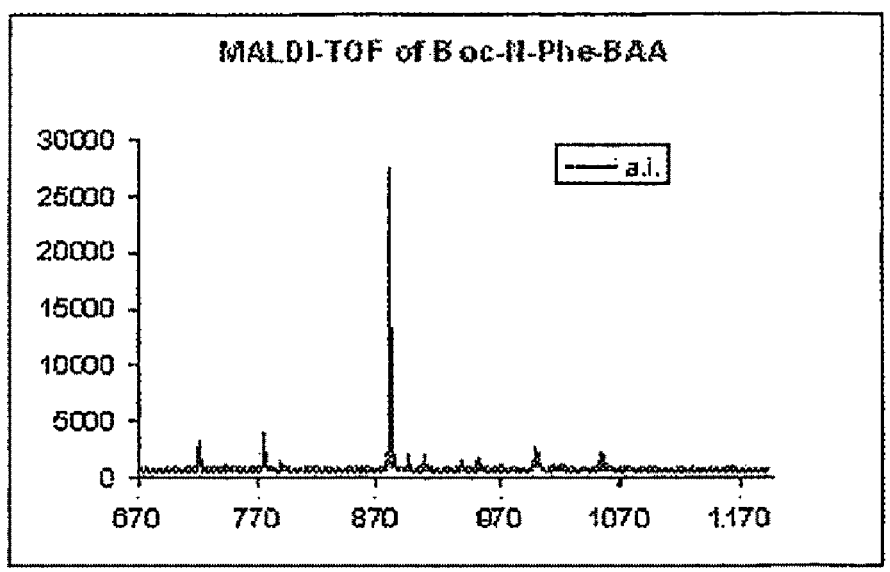
FIGS. 7A and 7B depict MALDI-TOF mass spectra of (A) Boc-protected 12 and (B) Fmoc-protected 12.
Figure 7:
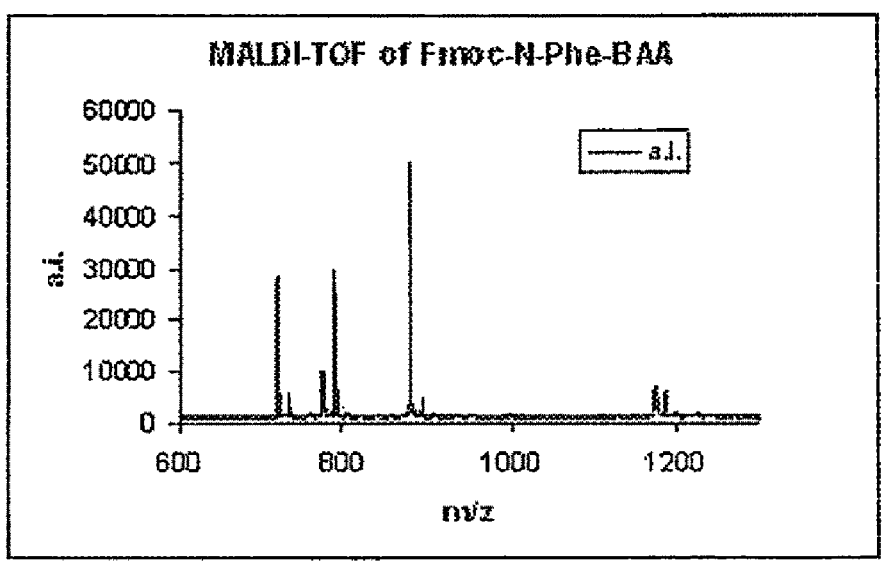

Variations on the above-described reaction scheme exist, some of which yield amino acid esters that must first be deprotected before they can be polymerized in peptide chains. Shown in FIG. 2 (Scheme 3) is the synthesis of N—Ac-Lys-OMe-BAA, wherein 1 is reacted with 7 to yield imine 8, which is then hydrogenated to yield N—Ac-Lys-OMe-BAA 9, where BAA="bucky amino acid" (i.e., a fullerene-based amino acid) This has been confirmed by MALDI-TOF-MS, as shown in FIG. 6. Alternatively, in some embodiments, it is desirable to protect only the carboxylic acid functionality or only the amino functionality, as shown in FIG. 3 (Scheme 4) for the synthesis of N-PG-Phe-OH-BAA, wherein 1 is reacted with 10 to yield imine 11 which is then hydrogenated to yield protected nano-amino acid 12, as confirmed by MALDI-TOF-MS (FIG. 7). Note that Boc=t-butoxycarbonyl and Fmoc=fluorenylmethoxycarbonyl.

As noted above, numerous medicinal and other biological applications exist for the nano- or fullerene-based amino acids of the present invention, and for amino acid residues comprising such fullerene-based amino acids. Such fullerene-based amino acids can be attached to or incorporated in various proteins. In some embodiments, these proteins are antibodies and the attached fullerene-based amino acid delivers a therapeutic or diagnostic agent to a target (mentioned previously herein). In other embodiments, these proteins are enzymes, and incorporation of fullerene-based amino acids into them alters their function (via structural alteration), i.e., turns them off, slows them down, speeds them up, or makes them perform an entirely different or related function. Furthermore, incorporation of such fullerene-based amino acids into proteins may serve in helping to elucidate structure-function relationships that are heretofore poorly understood.

In some embodiments, fullerene-based amino acids can be used to enlarge existing hydrophobic pockets within proteins, or create new ones. In such pockets, non-aqueous biological chemistry can take place. Increasing the volume of such pockets may increase the extent and type of this non-aqueous chemistry.

Figure 8:
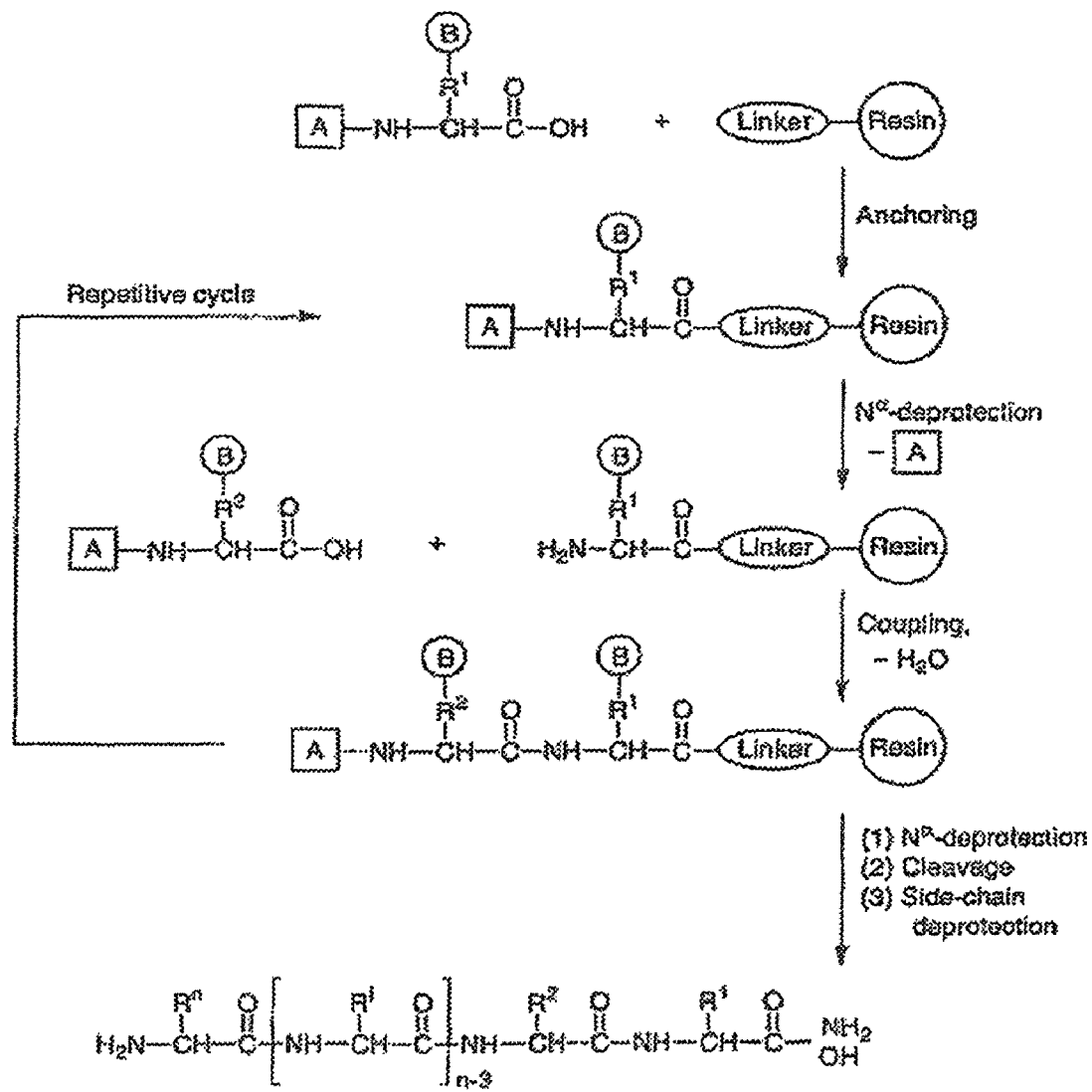
FIG. 8 depicts a solid-phase peptide chain synthesis according to an embodiment of the present invention.

In some embodiments, synthetic peptide chains are synthesized that comprise fullerene-based amino acids. These species may also be used to for diagnostic and therapeutic medical applications. In some embodiments, a sold-phase synthesis, like that shown in FIG. 8, is used to generate such synthetic peptide chains that comprise fullerene-based amino acids.

The following examples are included to demonstrate particular embodiments of the present invention. It should be appreciated by those of skill in the art that the methods disclosed in the examples that follow merely represent exemplary embodiments of the present invention. However, those of skill in the art should, in light of the present disclosure, appreciate that many changes can be made in the specific embodiments described and still obtain a like or similar result without departing from the spirit and scope of the present invention.

EXAMPLE 1

Synthesis of N—Ac-Fullerecine-Phe-OMe

Approximately 238 mg of buckyketone 1 (0.3 mmol), 85 mg Ac-Phe(4-$NH_2$)—OMe (0.36 mmol), and a catalytic amount of p-benzosulfonic acid were added to a 250 mL Schlenk flask equipped with a magnetic stir bar. The starting mixture was pumped dry under vacuum. Then, 150 mL degassed freshly distilled toluene was charged into the flask under an argon atmosphere. The flask was attached to a Soxhlet extractor filled with oven-dried 4 Å molecular sieve. The reaction mixture was refluxed overnight. After the heating was stopped, the dark, golden-brown solution was filtered by a cannula into a second Schlenk flask, also equipped with a magnetic stir bar. The resulting buckyimine solution was then hydrogenated by following a literature method See Lu et al., Tetrahedron Letters, 2002, 43, pp. 8617-8620.

After traditional work up, the solution was concentrated with a rotary evaporator and flash chromatographed on silica gel. The final product was eluted by toluene/MeOH (10:1).

EXAMPLE 2

Deprotection of N—Ac-Fullerecine-Phe-OMe

Approximately 50 mg N—Ac-Fullerecine OMe was added to a Schlenk flask equipped with a magnetic stir bar. The solid was degassed under vacuum and then dissolved in 25 mL $CH_2Cl_2$ and cooled to $-10°$ C. under an argon atmosphere. Approximately 5 mL of 1M $BBr_3$ in $CH_2Cl_2$ was added dropwise through a needle transfer with stirring. A dark brown precipitate resulted. Stirring continued at $-10°$ C. for 1 hr and at 25° C. for 2 hr. The reaction was quenched by the careful dropwise addition of 25 mL of water. The solids remained between the interface of the water and the $CH_2Cl_2$. The solids were centrifuged out, then washed with 6 M HCl (10 mL×2) with sonication. The residue was further washed with DI water (25 mL×3). The decanted liquid portion was a clear yellow solution that indicated that the produced fullerecine was soluble in $H_2O$. The solubility is estimated to be about 0.1 mg/mL.

EXAMPLE 3

Preparation of N—Ac-Fullerecine-Lys-OMe

Approximately 136 mg of buckyketone 1 (0.18 mmol), 70 mg Ac-Lys(4-$NH_2$)—OMe (0.36 mmol), and a catalytic amount of p-benzosulfonic acid were added to a 250 mL Schlenk flask equipped with a magnetic stir bar. This initial mixture was pumped dry under vacuum. Then, 150 mL of degassed, freshly distilled toluene/tetrahydrofuran (THF) (2:1) was charged into the flask under an argon atmosphere. The flask was attached to a soxhlet extractor filled with oven-dried 4 Å molecular sieve. The reaction mixture was refluxed overnight. After the heating stopped, the dark, golden-brown solution was filtered via cannula to a second Schlenk flask equipped with a magnetic stir bar. The resulting buckyimine solution was hydrogenated following a literature method. See Liu et al., Tetrahedron Letters, 2002, 43, pp. 8617-8620. Upon hydrogenation, a red-orange solid precipitated out and onto the flask surface. This precipitate was confirmed by MALDI-TOF-MS to be N—Ac-Fullerecine-Lys-OMe

EXAMPLE 4

Synthesis of N-Boc-Fullerecine-Phe-OH

Figure 9:
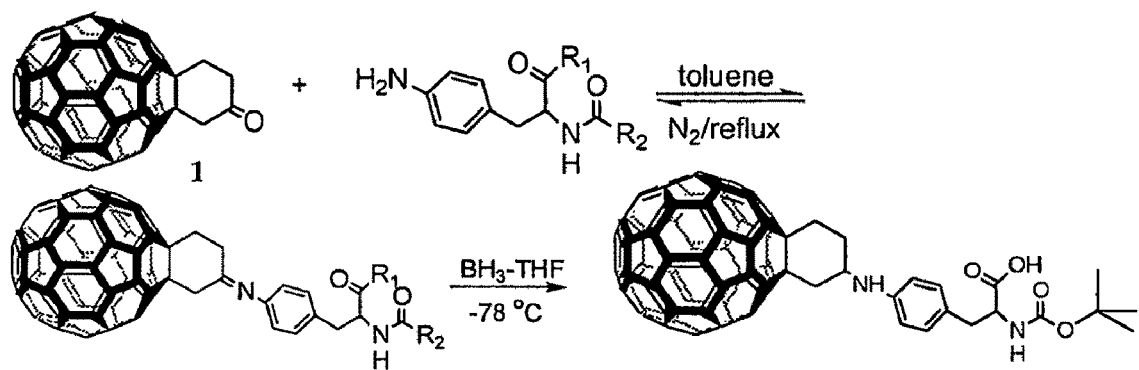
FIG. 9 depicts a synthesis of N-Boc-Fullerecine-Phe-OH according to another embodiment of the present invention.

The synthesis of N-Boc-Fullerecine-Phe-OH is depicted in FIG. 9. 238 mg of buckyketone 1 (0.3 mmol), 169 mg Boc-Phe(4-$NH_2$)—OH (0.6 mmol), and a catalytic amount of p-benzosulfonic acid were added into a 250 ml Schlenk flask equipped with a magnetic stir bar. The starting mixture was pumped dry under vacuum, after which 300 ml of degassed, freshly distilled toluene and 50 ml of dry THF were charged into the flask under an argon (Ar) atmosphere. The flask was headed on a Soxhlet extractor filled with oven dried 4 Å molecular sieve. The reaction mixture was refluxed for 2 days. In a second 250 ml flask, 100 mg of phthalic acid was added and dried in vacuo with a heat gun. The dried phthalic acid was then dissolved in 15 ml dry THF under Ar. After the Fullerene imine solution cooled down, the dark golden brown solution was filtered by cannula into a second Schlenk flask equipped with a magnetic stir bar. The resulting buckyimine solution was then cooled down to −42° C. in an acetonitrile/dry ice bath. Then, an excess amount (3 ml 1M) of $BH_3$-THF solution was injected into the flask by syringe. The reaction was completed after 2 hrs, as determined by a thin layer chromatographic (TLC) plate. Then, 2 ml of MeOH was injected to quench excess $BH_3$. The final solution was first washed with DI water, then dilute $KHCO_3$ solution carefully (to assure that the pH doesn't get too basic) to remove unreacted Boc-Phe(4-$NH_2$)—OH and phthalic acid. The solution was concentrated on a rotary evaporator (rotovap) and flash chromatographed on silica gel. 167 mg of the final product was eluted by toluene/ethyl acetate/$CH_3COOH$ (100:7:0.8).

EXAMPLE 5

Synthesis of N-Fmoc-Fullerecine-Phe-OH

Figure 10:
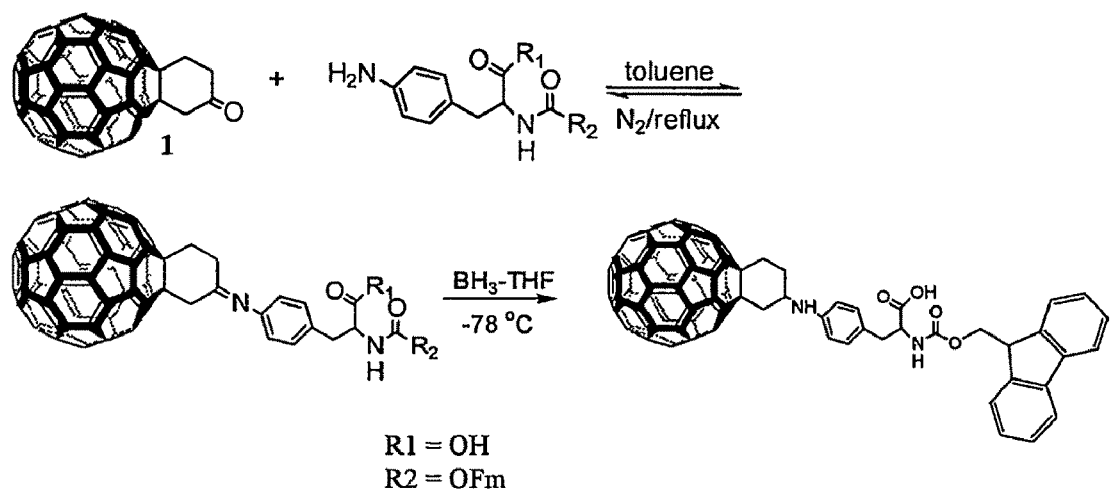
FIG. 10 depicts a synthesis of N-Fmoc-Fullerecine-Phe-OH according to another embodiment of the present invention.

The synthesis of N-Fmoc-Fullerecine-Phe-OH is depicted in FIG. 10. 316 mg of buckyketone 1 (0.4 mmol) and 412 mg Fmoc-Phe(4-$NH_2$)—OH (0.6 mmol) and catalytic amount of p-benzosulfonic acid were added in a 250 ml Schlenk flask equipped with a magnetic stir bar. The starting mixture was pumped dry under vacuum, after which 300 ml of degassed, freshly distilled toluene and 100 ml dry ethyl acetate were charged into the flask under an argon atmosphere. The flask was headed on a Soxhlet extractor filled with oven dried 4 Å molecular sieve. The reaction mixture was refluxed for 2 days. In a second 250 ml flask, 100 mg of phthalic acid was added and dried in vacuo with heat gun. The dried phthalic acid was then dissolved in 15 ml dry THF under Ar. After the Fullerene imine solution cooled down, the dark golden brown solution was filtered by a cannula to a second Schlenk flask equipped with a magnetic stir bar. The resulting buckyimine solution was then cooled down to −42° C. with all acetonitrile/dry ice bath. Then excess amount (3 ml 1M) $BH_3$-THF solution was injected by syringe. The reaction was complete after 3 hrs, as shown by TLC plate. Then, 2 ml of MeOH was injected to quench excess $BH_3$. The final solution was first washed with dilute $KHCO_3$ solution to carefully adjust the pH to 7, then with dilute HCl to remove unreacted Fmoc-Phe(4-$NH_2$)—OH and phthalic acid. The solution was concentrated on a rotovap and flash chromatographed on silica gel. 195 mg of the final product was eluted by toluene/ethyl acetate/$CH_3COOH$ (100:8:1).

EXAMPLE 6

Synthesis of Fullerene Peptide II (BAA-Glu-Glu-Glu-Glu-Gly-Gly-Gly-Ser-COOH) (SEQ ID NO. 1)

The couplings of first 7 residues after serine of fullerene peptide II (SEQ ID NO. 1) were carried out on an automated APEX 396 Multiple Peptide Synthesizer (Advanced ChemTech) under nitrogen flow. 430 mg (0.3 mM) Fmoc-serine-rink resin was used as solid phase. Each coupling uses 4-fold amino acid excess, and HBTU, HOBT as activators and DIEA as base in a 1:1:1:3 ratio. Fmoc deprotection was performed using 20% piperidine in DMF solution. After the deprotection of the eighth residue (Glu) was finished, one sixth of the resin was moved out to a 25 ml fritted glass tube, wherein the resin was swollen with DMF. A 3-fold excess of BocBAA was then dissolved in 9 ml DMF/DCM (2:1). The Boc BAA solution was first activated with PyBOP/HOBT/DIEA (1:1:1:3) for 2 minutes. The activated Boc BAA was mixed with the resin in the fritted glass tube, and shaken on an automated shaker for 1 day at room temperature. Then, the resin was washed thoroughly with DMF and $CH_2Cl_2$ to remove unreacted FmocBAA. The final peptide was cleaved twice from the solid support using 10 ml TFA:TISP:$H_2O$ (98:1:1) for 4 hrs and 18 hrs. The crude fractions were washed with diethyl ether and lyophilized to remove TFA.

EXAMPLE 7

Cell Viability Assay or Evaluation of the Cytotoxicity of Fullerene Peptide

Rat maxillary incisor pulp cells (RPC-C2A) were seeded on a 24-well tissue culture plate at 3540 cells per well and incubated for 24 hr at 37° C. in a 5% $CO_2$ environment. Dulbecco's Modified Eagle's Medium (DMEM; Invitrogen, NY) was prepared with 10% fetal bovine serum (FBS; Bio-Whitaker, Walkersville, Md.), 2 mM Amphothericin B, 1 unit/ml penicillin, and 100 mg/l streptomycin (Invitrogen, NY). Three different concentrations of Fullerene peptide solutions (4, 40, and 400 µM) were prepared in PBS and sterilized using 0.2 µm filter syringe. 100 µL of the solution was mixed with 1.9 mL of medium and added to cells. Control was also prepared by adding PBS buffer solution without peptide-modified fullerene to cells. After 48 hrs of incubation, cell viability was determined using Live-Dead Assay Kit (Molecular Probes, Inc., Eugene, Oreg.). Calcein AM is converted to a green fluorescent product within live cells due to enzymatic activity, while ethidium homodimer-1, a red fluorescent compound, accumulates in dead cells due to increased membrane permeability. After removing medium, cells were rinsed with PBS solution twice. Cells in each well was incubated with 0.4 mL of 4 µM EthD-1 and 2 µM of Calcein AM in PBS for 30 min and observed under fluorescent microscope.

Figure 11:
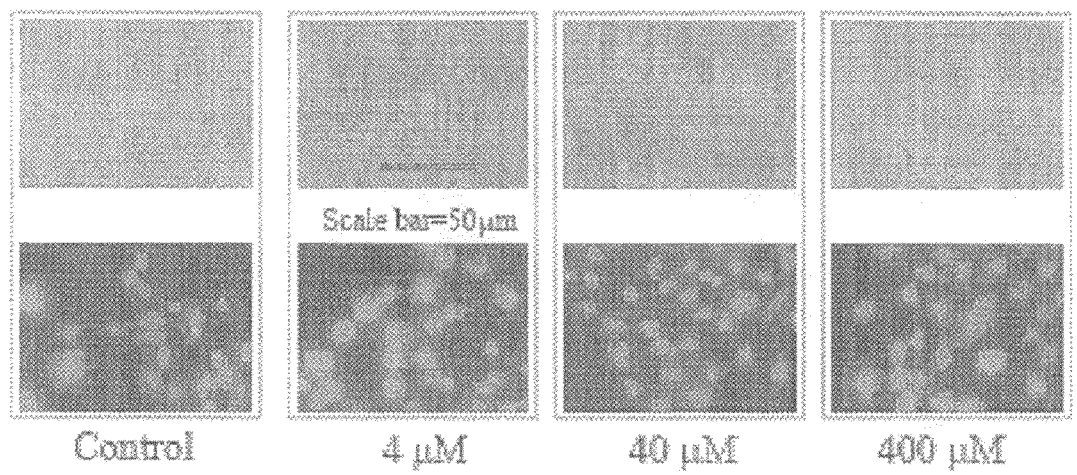
FIG. 11 depicts phase contrast microscope (top) and fluorescent microscope images for a cell viability test using a fullerene peptide made according to an embodiment of the present invention.

FIG. 11 depicts the phase contrast microscope (top) and fluorescent microscope (bottom) images for the cell viability test. The cells continued to fluoresce green indicating that they were still alive. The cell viability test reflects that the fullerene-based peptide shows no toxicity to the cells.

Figure 12:
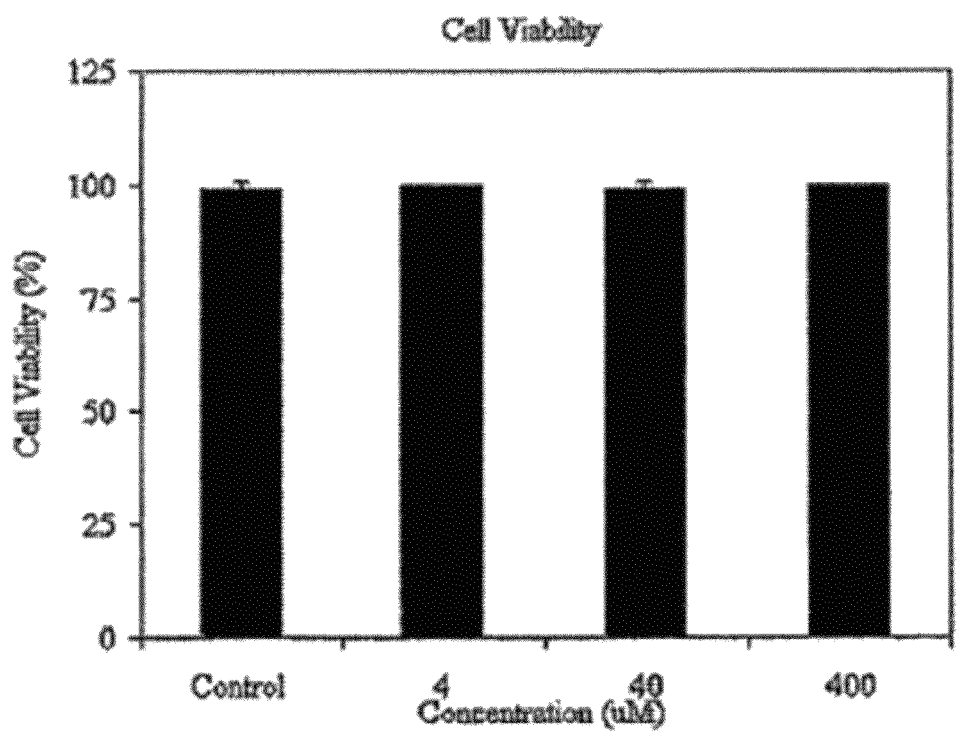
FIG. 12 depicts the statistical analysis of the cell viability evaluation.

For the statistical analysis, the data were compared with two-tailed, unpaired t-tests. P-values less than 0.05 were considered to be significant. Data are presented as mean±standard deviation. This statistical analysis is shown in FIG. 12.

All patents and publications referenced herein are hereby incorporated by reference. It will be understood that certain of the above-described structures, functions, and operations of the above-described embodiments are not necessary to practice the present invention and are included in the description simply for completeness of an exemplary embodiment or embodiments. In addition, it will be understood that specific structures, functions, and operations set forth in the above-described referenced patents and publications can be practiced in conjunction with the present invention, but they are not essential to its practice. It is therefore to be understood that the invention may be practiced otherwise than as specifically described without actually departing from the spirit and scope of the present invention as defined by the appended claims.

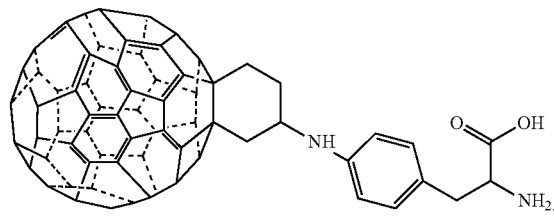

3. The amino acid composition of claim 1, wherein both the amine functionality and the carboxylic acid functionality on the amino acid composition are protected, and wherein the amino acid has a general formula of —HN—CH(R)—C(O)—O—.

4. The amino acid composition of claim 1, wherein one of either the amine functionality or the carboxylic acid functionality on the amino acid composition is protected, and wherein the amino acid composition has a general formula of —HN—CH(R)—C(O)—OH or H₂N—CH(R)—C(O)—O—.

5. The amino acid composition of claim 4, wherein the amine functionality is protected with a protecting group selected from the group consisting of Boc, Fmoc, and combinations thereof.

6. The amino acid composition of claim 1, wherein the fullerene species is endohedrally-doped with a species selected from the group consisting of radioactive species, non-radioactive species, metals, gases, spin ½ nuclei, and combinations thereof.

7. A synthetic polymer comprising an amino acid composition, wherein the amino acid composition has a general formula of one of H₂N—CH(R)—C(O)—NH— or —HN—CH(R)—C(O)—NH—, and wherein the R functionality comprises a fullerene species derived from a buckyketone.

8. The synthetic polymer of claim 7, further comprising at least one naturally occurring amino acid.

What is claimed is:

1. An amino acid composition having a general formula of one of H₂N—CH(R)—C(O)—OH, —HN—CH(R)—C(O)—OH, H₂N—CH(R)—C(O)—O—, or —HN—CH(R)—C(O)O—, wherein the R functionality comprises a fullerene species derived from a buckyketone.

2. The amino acid composition of claim 1, wherein said amino acid composition comprises the following compound:

9. The synthetic polymer of claim 7, wherein the synthetic polymer is selected from the group consisting of peptide chains, polypeptides, and proteins.

10. The synthetic polymer of claim 7, wherein the synthetic polymer is a protein exhibiting a biological function selected from the group consisting of enzymatic functions, antibody functions, oxygen transport, ion transport, and combinations thereof.

11. The synthetic polymer of claim 7, wherein the fullerene species provides for reaction "pockets" within said polymer.

12. The synthetic polymer of claim 7, wherein the fullerene species serves as a link between at least two amino acids.

13. A method comprising the steps of:
a) reacting the following compound

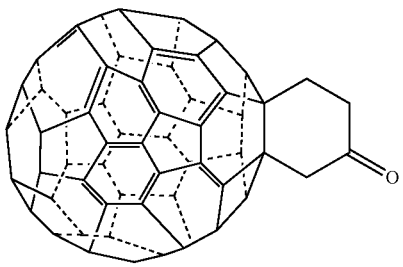

with a compound selected from the group consisting of:

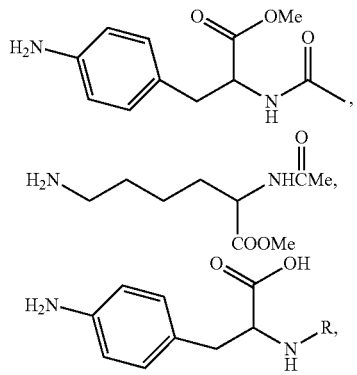

wherein R is a protecting group,
and combinations thereof to yield an imine intermediate; and
b) hydrogenating the imine intermediate with BH$_3$-THF to yield at least one product selected from the group consisting of

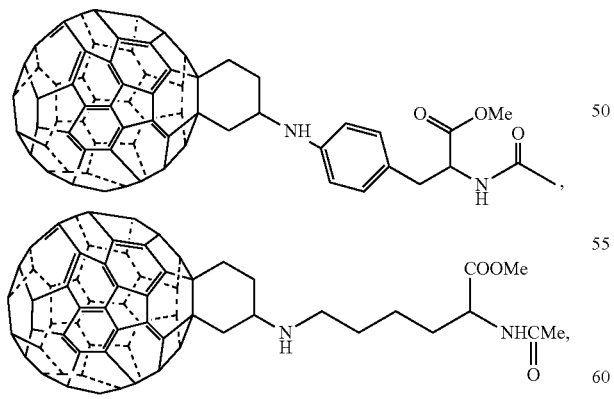

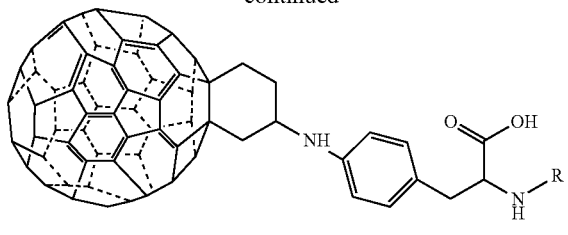

wherein R is a protecting group,
and combinations thereof.

14. The method of claim 13, further comprising a deprotection step.

15. The method of claim 14, wherein the method yields the following compound:

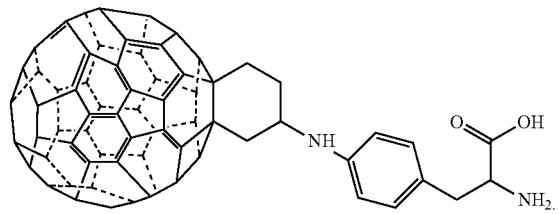

16. The method of claim 13, wherein the protecting group is Boc.

17. The amino acid composition of claim 1, wherein the buckyketone comprises the following compound:

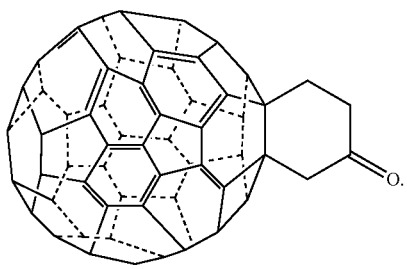

18. The synthetic polymer of claim 7, wherein the buckyketone comprises the following compound:

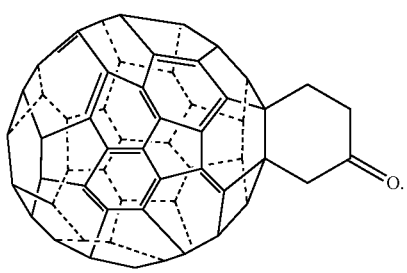

* * * * *